United States Patent [19]

Welch et al.

[11] Patent Number: 4,790,610

[45] Date of Patent: Dec. 13, 1988

[54] MEDICAL EMERGENCY CRASH CART

[75] Inventors: Robert J. Welch, Dallas; Albert Kolvites, Mountaintop; Robert M. White, Conyngham, all of Pa.

[73] Assignee: InterMetro Industries Corporation, Wilkes-Barre, Pa.

[21] Appl. No.: 901,056

[22] Filed: Aug. 26, 1986

[51] Int. Cl.[4] .............................................. E05B 53/00
[52] U.S. Cl. ................................... 312/218; 312/216; 312/209
[58] Field of Search ............... 312/209, 216, 217, 218, 312/107.5, 222, 250

[56] References Cited

U.S. PATENT DOCUMENTS

| | | | |
|---|---|---|---|
| 224,294 | 2/1980 | Koch | 312/216 |
| 1,424,531 | 8/1922 | Turbeville | 312/216 |
| 2,286,427 | 6/1942 | Levensten | 312/222 |
| 2,440,541 | 4/1948 | Gash | 312/217 |
| 3,428,383 | 2/1969 | Nobel | 312/209 |
| 3,969,006 | 7/1976 | Brown | 312/209 |
| 4,583,795 | 4/1986 | Brown et al. | 312/209 |
| 4,616,891 | 10/1986 | Jantzen | 312/216 |

FOREIGN PATENT DOCUMENTS 1144064 2/1963 Fed. Rep. of Germany .

OTHER PUBLICATIONS

Emergency Trolley EMT 300/2, S&W Teknik, A/S, Denmark Mehrzweckwagen, Denmark, pp. 14, 18, 31.

Primary Examiner—Kenneth J. Dorner
Assistant Examiner—Gerald Anderson
Attorney, Agent, or Firm—Fitzpatrick, Cella, Harper & Scinto

[57] ABSTRACT

A medical emergency crash cart includes a housing having a top formed with a recessed tray for storing instruments, supplies, and the like, and at least one side formed with an opening. A transparent cover selectably covers the tray but provides visual access to its contents. A removable door encloses the opening. At least one storage compartment is mounted on another side of the housing and is pivotable between open and closed positions. A single latch mechanism simultaneously locks the cover in position covering the tray, the door in position enclosing the opening in the housing, and the compartment in its closed position.

38 Claims, 9 Drawing Sheets

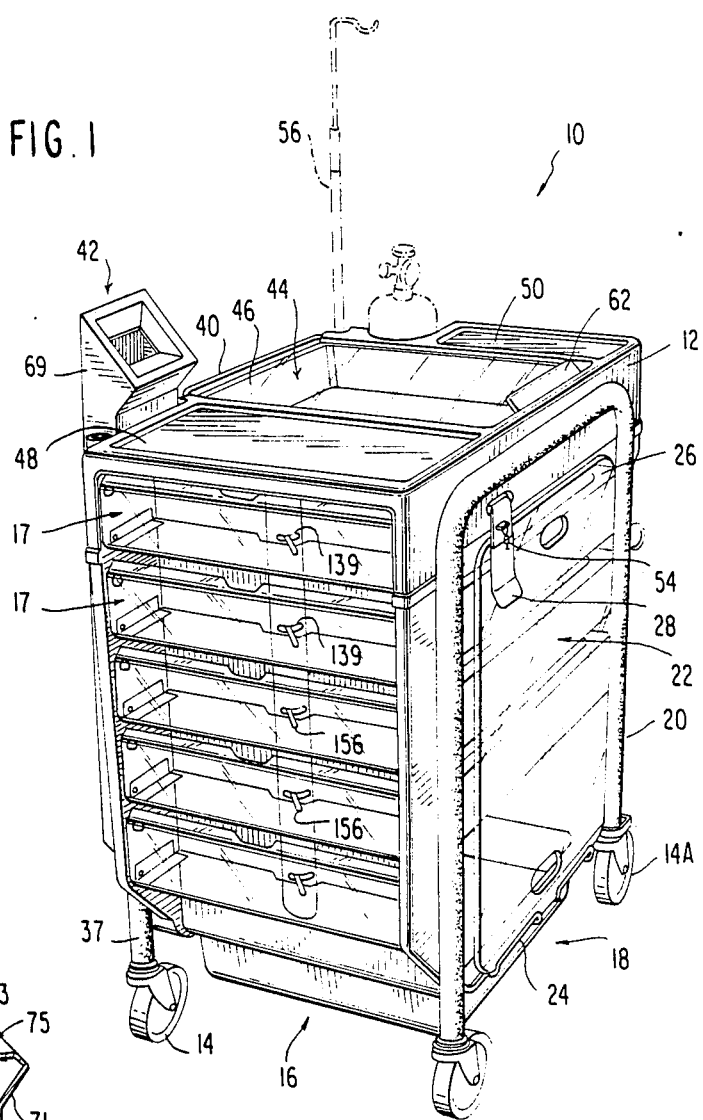
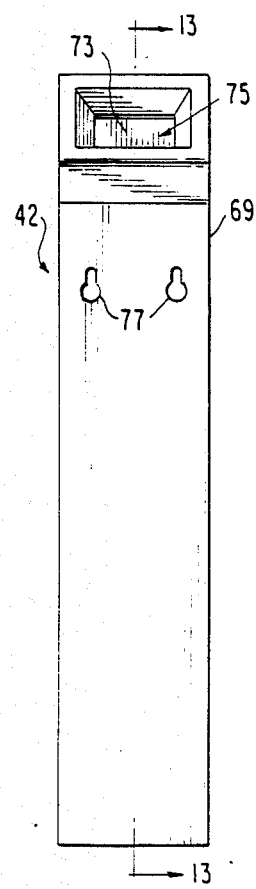
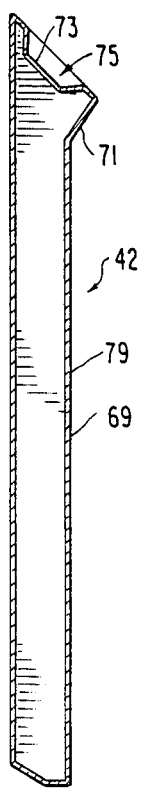
FIG. 1
FIG. 12
FIG. 13

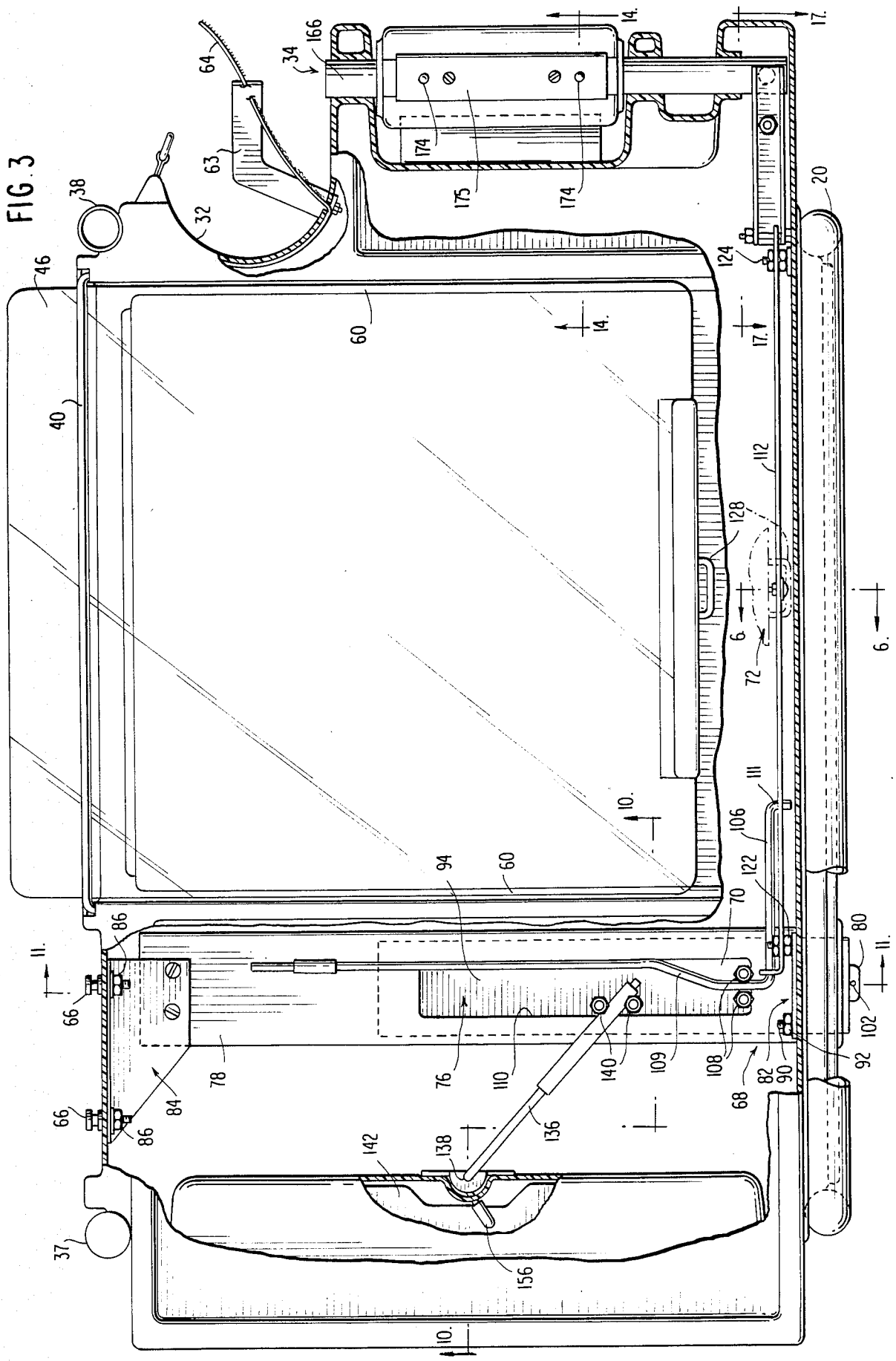

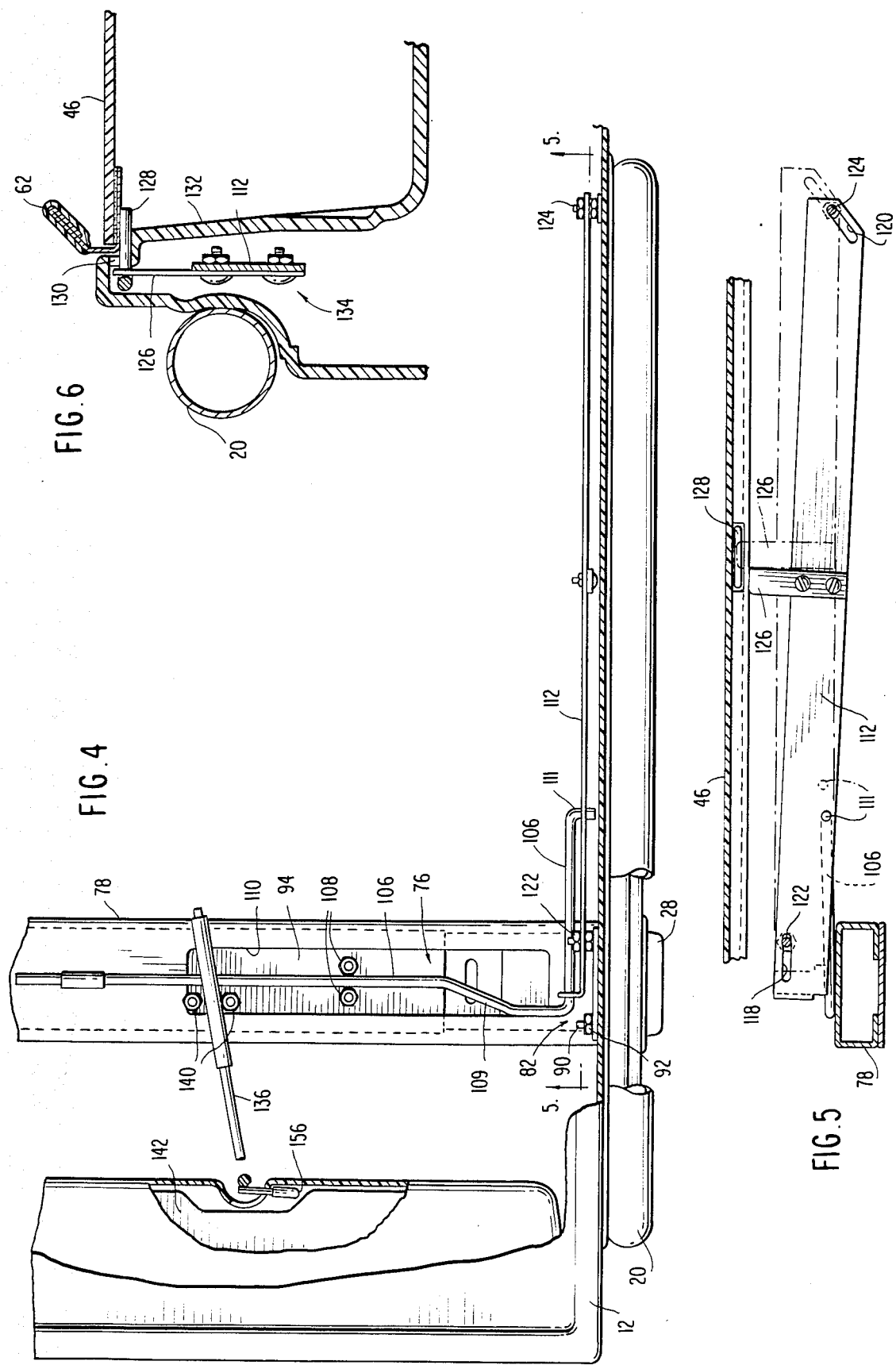

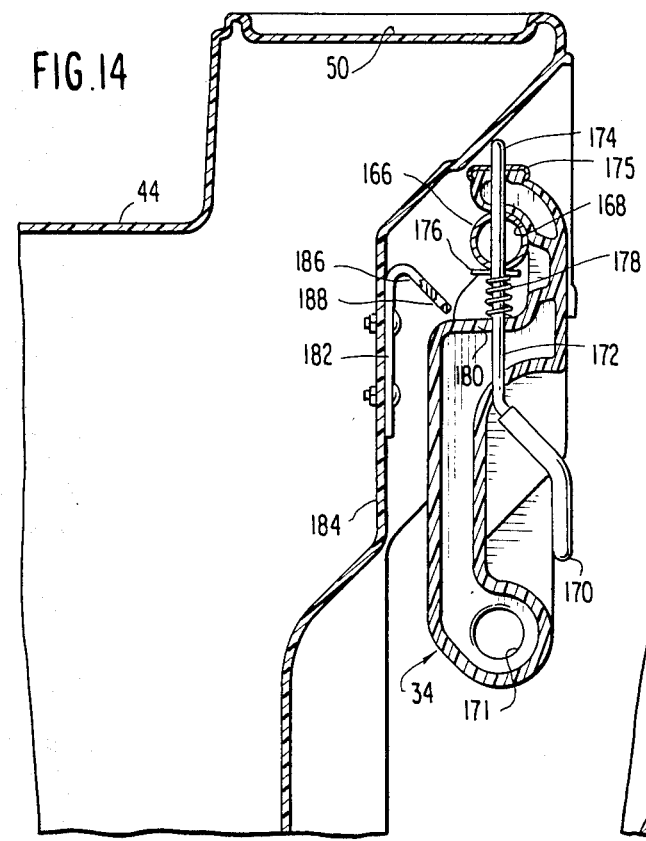
FIG.14
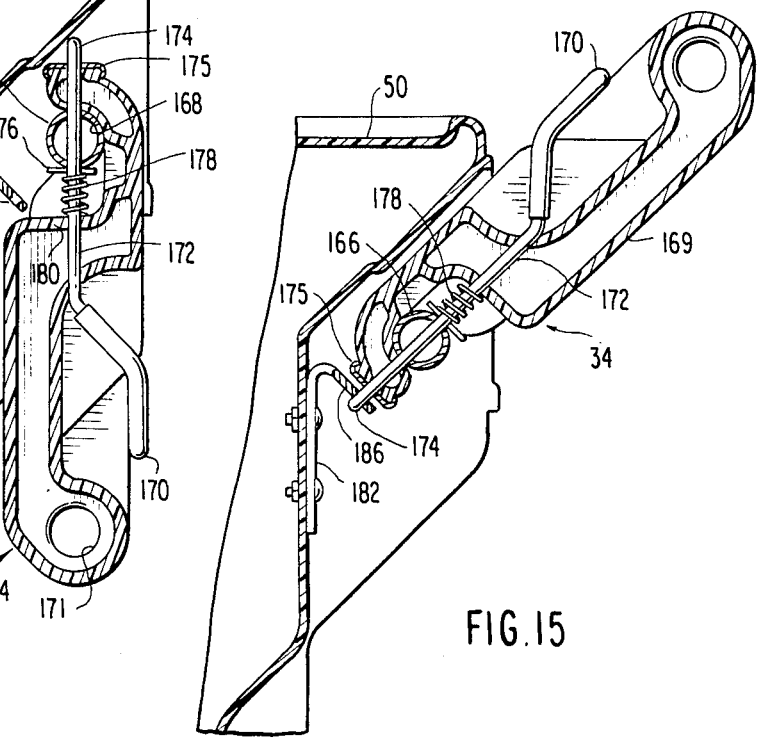
FIG.15
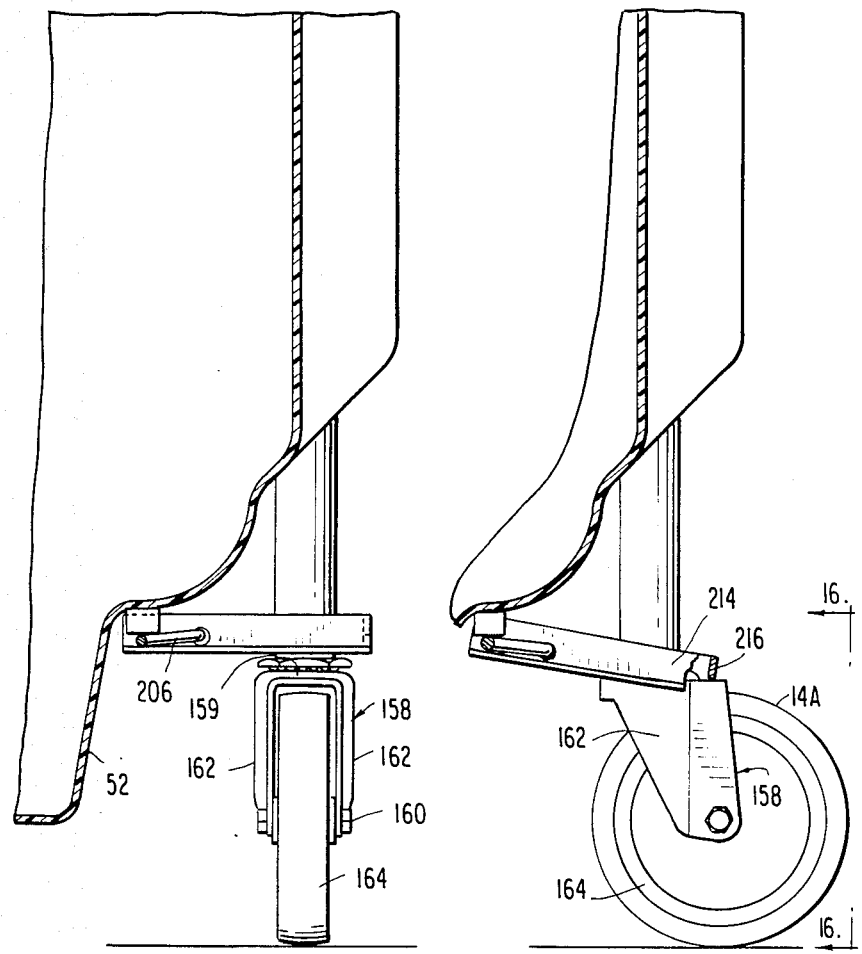
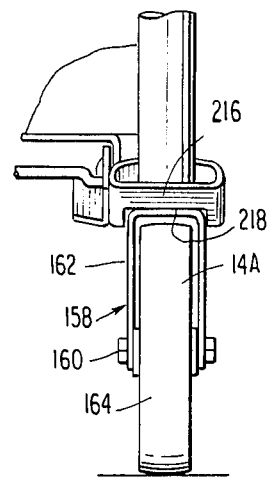
FIG.16

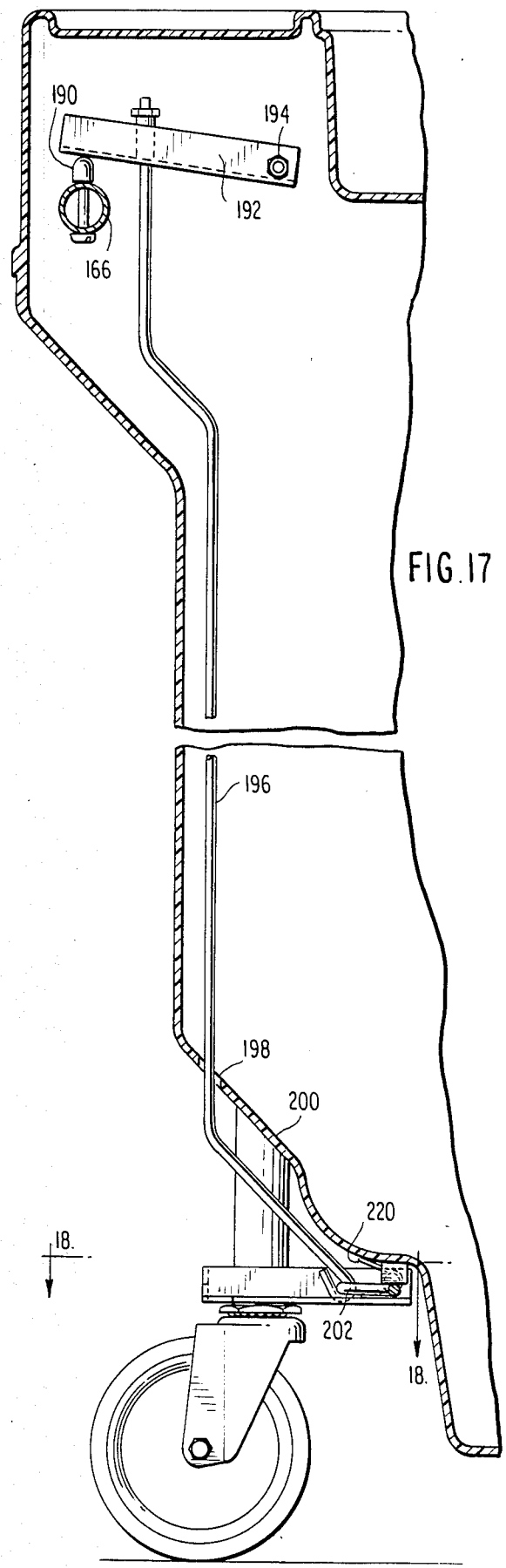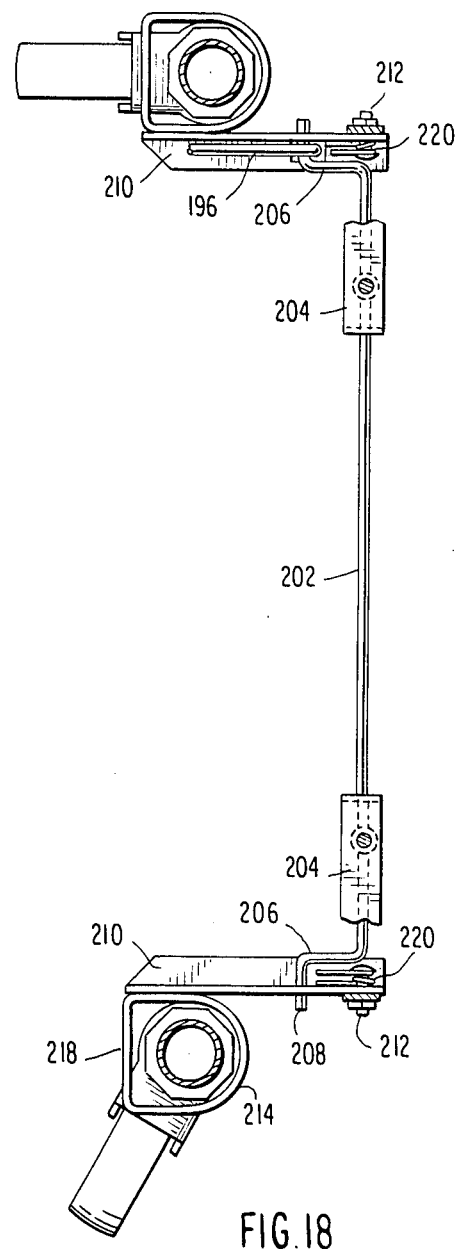

ately equipped 4,790,610

MEDICAL EMERGENCY CRASH CART

BACKGROUND OF THE INVENTION

1. Field of the Invention

The present invention relates to a mobile cart, and more particularly to a mobile cart commonly called a "medical emergency crash cart" or simply a "crash cart", for medical emergency use in hospitals and other medical institutions. The crash cart of the present invention includes direction-locking casters for improved high speed stability and maneuverability and a common security latch mechanism for simultaneously securing all compartments of the crash cart in a sealed condition, indicating that the crash cart contains a full complement of readily accessible medical equipment, instruments, and supplies.

2. Description of the Prior Art

A medical emergency crash cart commonly contains the medical equipment, instruments, and supplies that are necessary particularly for medical procedures practiced in cases of cardiac emergencies. However, the crash cart may be equipped for any type of medical emergency. The crash cart generally includes a housing having a plurality of drawers, shelves, and/or compartments for storing medical equipment and supplies such as syringes and drugs. The housing is supported by a plurality of wheels or casters so that it may be moved rapidly from its place of storage to the place of the medical emergency. To provide maximum efficiency during a medical emergency, a crash cart must therefore provide both (1) agile and stable mobility and (2) efficient storage with immediate visual and physical accessibility to and organization of all medical equipment, instruments, and supplies.

One drawback of current crash carts is the loss of stability during high speed travel. First, as a crash cart must be able to maneuver quickly in small areas of patient's or hospital emergency rooms, it is desirable to support the housing on swivel casters. Second, as medical equipment, instruments, and supplies are expensive, each hospital maintains only a limited number of crash carts (e.g. one crash cart per floor or station). Therefore, when a medical emergency occurs, a crash cart operator must rush the cart through the hospital corridors often over relatively long distances to the patient. However, swivel casters may cause the cart to be difficult to steer at high speeds particularly when an attempt is made to change the direction of movement, for example, by going around corners in corridors or turning into the patient's room. Therefore, the crash cart operator must either reduce his speed through the halls or risk overturning the cart. The risk of overturning increases when the operator must negotiate the cart around a corner, as swivel casters do not provide a firm pivot about which to turn but rather permit inertia of the cart to cause it to tend to continue to move in its original direction. Alternatively, a crash cart may be operated by two persons. However, this is less efficient and may in fact not be possible during any given emergency.

Another drawback of current crash carts is that they provide inefficient storage and accessibility of medical emergency items. An important characteristic of a crash cart is the physical accessibility of the medical equipment, instruments, and supplies stored in it. Immediate accessibility to each item is desired when administering emergency care. In current crash carts, however, a "med tray" (containing syringes and drugs such as ampules of adrenolin, and the like) is typically contained in a drawer within the cart. Storage of all supplies in drawers may make administration of care at the emergency scene difficult because access may only be had to one drawer at a time.

Still a further drawback of current crash carts is the limited ability to visually inspect the medical equipment, instruments and supplies easily and prior to an emergency. Generally, it is important that a crash cart always be fully equipped since if one or more items is missing when an emergency occurs, medical professionals using the cart may not be able to successfully treat the patient. However, for a number of legitimate reasons, individual items are often taken in haste from a crash cart during non-emergency conditions. Each cart must therefore be periodically inspected (e.g. each day or each shift) to insure that it is fully stocked. In light of the large number of items contained therein, it is an inefficient use of hospital time and personnel to physically inspect fully stocked crash carts. The ability to secure and to visually inspect a crash cart, to assure that a full complement of the critical instruments and supplies are contained therein, is therefore highly desirable.

For these and other reasons, the crash carts of the prior art are not entirely satisfactory. A need exists for an improved crash cart having greater high speed stability and maneuverability, greater accessibility to the contents thereof, and a security system for maintaining and assuring maintenance of a full complement of medical equipment, instruments, and supplies therein.

SUMMARY OF THE INVENTION

It is therefore an object of the present invention to increase the stability and maneuverability of a crash cart when moving at high speeds, particularly when maneuvering around corners, while retaining the benefits of agility in close quarters.

It is another object of the present invention to improve the accessibility of medical equipment, instruments, and supplies in a medical emergency crash cart.

It is yet another object of the present invention to provide a security mechanism that offers easy visual inspection of at least most of the critical contents of the crash cart and that assures that a full complement of medical equipment, instruments, and supplies are stored within the crash cart.

These objects and further advantages are achieved by the present invention, which is an improved crash cart having means for locking at least one of a plurality of swivel casters supporting the crash cart in a single direction of travel, a readily accessible med tray recessed in the top surface of the cart, and a common security latch mechanism for securing all medical equipment, instrument, and supply compartments thereof.

More particularly, the crash cart of the present invention includes a mechanism for locking two of four swivel casters, supporting a housing of the cart, for rolling movement in parallel planes with their axes of rotation mutually parallel. Locking of these casters is quickly accomplished by manipulating a handle for steering the cart in the direction of desired movement. When the lockable casters swivel to their position in the direction of desired movement they are automatically locked in place by the locking mechanism. Therefore, these locked casters can become pivots about which the cart can be turned when it is necessary to change direction. Further, by second manipulation of the handle, locking of the two casters can be quickly released so that all casters can swivel and the cart can be easily manuevered into tight spaces.

The housing of the crash cart is molded with an integral med tray in its top. The med tray is covered by a transparent cover providing easy visual inspection of the tray's contents. Items stored in the tray are those most frequently needed in an emergency. Therefore, the tray and at least one drawer accessible from the front of the cart may be simultaneously opened such that the contents of both are simultaneously available. Storage areas on another side of the cart may also be accessible at the same time. Other less frequently used supplies may be stored in more conventional drawers which are accessible from a side of the cart and which are also covered by a transparent panel.

The cover of the top med tray as well as drawers accessible from a side of the cart and other essential supplies are all secured in locked condition by a common latching mechanism. A breakable seal provided on the latching mechanism can provide quick visual confirmation that, if unbroken, the complements of the cart are complete. The latching mechanism is designed to easily shear the seal.

A more complete appreciation along with an understanding of other objects, features, and aspects of the present invention will become apparent from the following detailed description when considered in conjunction with the accompanying drawing.

BRIEF DESCRIPTION OF THE DRAWINGS

FIG. 1 is a right-front perspective view of the preferred embodiment of a crash cart in accordance with the present invention;

FIG. 3 is a plan view, partially in cross-section and broken away to show internal detail, of the top of the crash cart illustrated in FIGS. 1 and 2 showing the common latching mechanism in locked condition;

FIG. 4 is a partial plan and broken away view similar to FIG. 3, of the common security latch mechanism of FIG. 3 in the unlocked condition;

FIG. 5 is a vertical cross-sectional view taken on plane 5—5 in FIG. 4 of the security latch mechanism illustrated in FIGS. 3 and 4;

FIG. 6 is a vertical cross-sectional view taken on plane 6—6 in FIG. 5, showing further details of the latch mechanism;

FIGS. 12 and 13 are respectively a front view and a vertical cross-sectional view taken on plane 13—13 in FIG. 12 of a disposable waste container for the preferred embodiment of the present invention;

FIG. 14 is a vertical cross-sectional view taken on plane 14—14 in FIG. 3 of a handle for steering the crash cart of the present invention and for locking two swivel casters to provide directional stability for high speed movement;

FIG. 15 is a view similar to FIG. 14 showing the handle in position to lock the casters;

FIG. 16 is a rear view of the caster direction-locking mechanism taken in the direction 16—16 of FIG. 15;

FIG. 17 is a view similar to FIG. 14 showing how movement of the handle is transmitted to unlock the two swivel casters; and FIG. 18 is a horizontal cross-sectional view taken on plane 18—18 in FIG. 17 showing further details of the caster direction locking mechanism.

DETAILED DESCRIPTION OF THE PREFERRED EMBODIMENT

Figure 2:
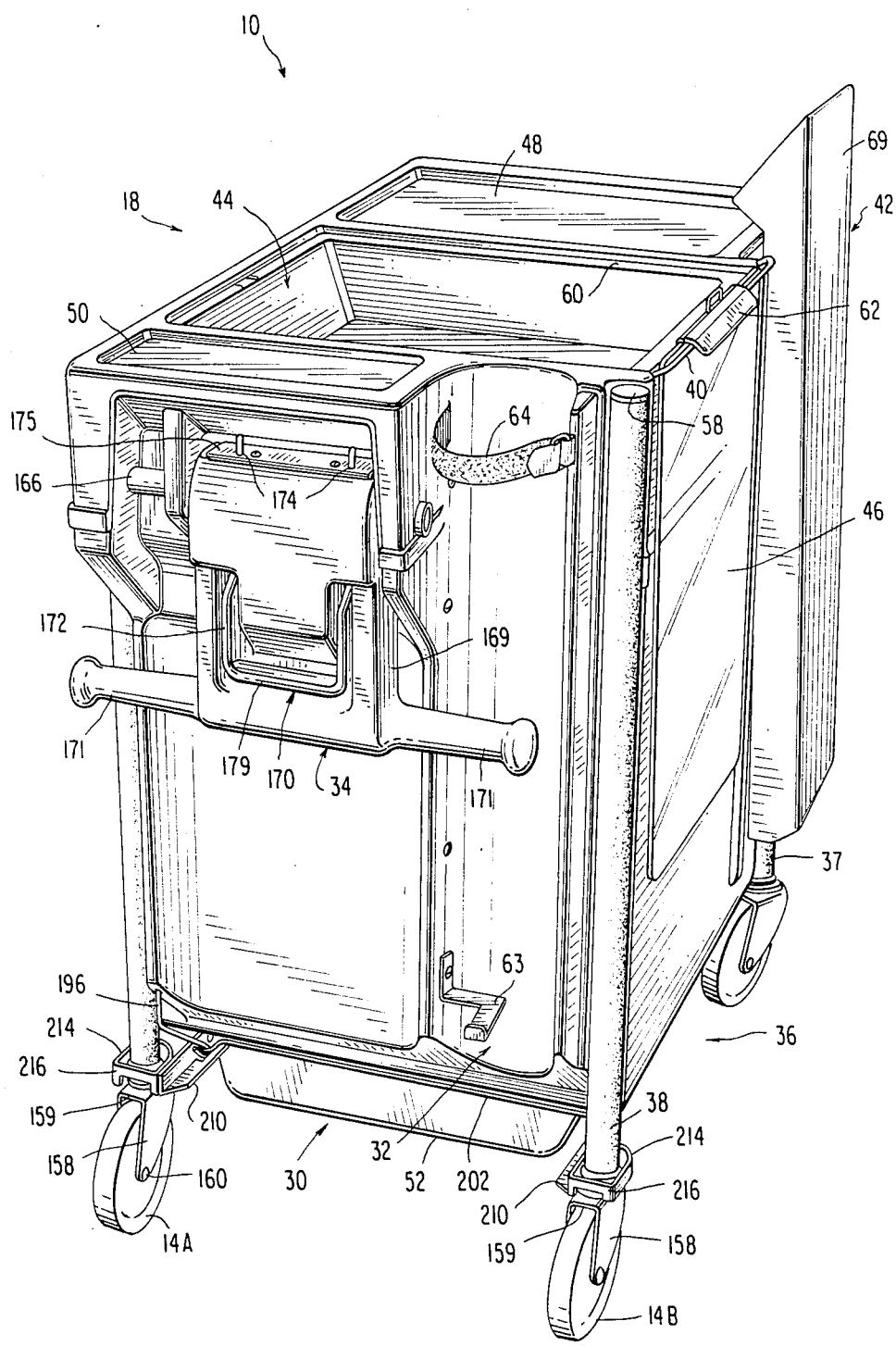
FIG. 2 is a left-rear perspective view of the preferred embodiment of a crash cart in accordance with the present invention.

Referring now to the drawing, FIGS. 1 and 2 illustrate the preferred embodiment of the emergency medical crash cart of the present invention in right-front and left-rear perspective views, respectively. The crash cart 10 includes a generally cubic housing 12 supported by four casters 14 disposed near the lower four corners of the housing in order to provide wide wheel bases in front to rear and side to side directions. For the purpose of description, the various sides of the crash cart will be designated as follows: a front side 16 from which are accessible a plurality of I.V. solution compartments 17; a right side 18 from which is seen a U-tube 20, an opening 22 in the housing 12, a door or back board support bracket 24, a transparent cardiac back board 26 or removable door supported at a bottom edge by the bracket 24, and a security latching mechanism locking plate 28; a rear side 30 having an oxygen tank compartment 32 and an operator's steering handle 34; and a left side 36 comprising a front support tube 37, a rear support tube 38, a med tray cover hanger 40 and a disposable container 42 for refuse. The top of the crash cart comprises a recessed med tray compartment 44, a med tray compartment cover 46, a large recessed prep area 48, and a small prep area 50. The bottom of the crash cart comprises an open-top equipment compartment 52, which depends from the housing 12 between the casters 14 and is accessible from the opening 32 in the right side of the cart 10.

The crash cart 10 is generally composed of lightweight materials. The housing 12 may be composed of plastic, preferably a thermoplastic such as polyethylene, and may be formed by a conventional process such as rotational molding. The U-tube 20 defines the opening 22 in the right side 18 of the crash cart 10, and provides structural support therefor. The tube is therefore preferably composed of steel. The front and rear support tubes 37 and 38 on the left side 36 of the crash cart 10 likewise provide structural support for the housing and are therefore also preferably composed of steel tubing. The U-tube and support tubes are affixed to the housing by conventional means such as bolts or other suitable structures. The placement of the other support tubes provides a broad wheel base for the cart to enhance its stability. The plastic housing 12 may further be molded to cooperate with the support tube geometry, thereby increasing the structural rigidity of the crash cart. The med tray compartment cover 46, cardiac back board 26, and I.V. compartments 17 are preferably composed of a rigid transparent, translucent or tinted plastic to facilitate visual inspection of the tray 44 and the interiors of the housing 12.

FIG. 1 illustrates the crash cart in a secured, emergency-ready state. For purposes of illustrating the features of the cart, all medical equipment, instruments and supplies normally present are not shown. All compartments of the crash cart are secured by a common security latch mechanism, to be described in detail below. The lock plate 28 is shown secured by a breakable seal 54, indicating that all crash cart compartments are secured, and have not been tampered with. Assuming that the cart was fully stocked when secured, a visual inspection of the seal 54 therefore quickly assures hospital personnel that the crash cart contains a full complement of medical emergency equipment, instruments, and supplies, avoiding unnecessary periodic physical inspections that otherwise would require opening of all compartments of the cart.

FIGS. 1 and 2 illustrate further features of the present invention. As shown in phantom lines in FIG. 1, a conventional telescoping I.V. stand 56 may be mounted on the cart by inserting the stand into the rear support tube 38. The front support tube 37 may be similarly used, or alternatively used as a stand for holding a rotating platform (not shown), such as a difibrilator platform. When not used as described, the support tubes 37 and 38 may be capped with a plastic or rubber cap 58, as shown in FIG. 2.

FIG. 2 illustrates the crash cart 10 in an unsecured state for emergency administration of treatment. The med tray compartment cover 46 is normally supported by a lip 60 around the periphery of the med tray compartment 44, and is securely held thereon by a med tray compartment cover security latch mechanism (to be described in detail below) in cooperation with the med tray compartment cover hanger 40 as can be seen in FIG. 1. When the security latch mechanism is released, the med tray compartment cover 46 may be slid off the left side 36 of the cart 10 beneath the med tray compartment cover hanger 40, dropped to that side, and hung on the hanger 40 by means of a hanger flange 62 secured to one side of the cover 46. In this manner, the med tray compartment cover 46 may be quickly and efficiently stored during medical emergency administration.

FIGS. 1 and 2 further illustrate the operator's steering handle 34 and directional locking caster mechanism (to be described in detail below) in an unlocked state. This mechanism in this state allows both the front and rear casters 14 to swivel freely, providing maximum maneuverability in tight quarters.

FIG. 3 is a plan view of the top of the crash cart 10 illustrated in FIGS. 1 and 2, portions thereof having been cut-away to illustrate the common security latch mechanism, the operator s steering handle and caster direction-locking mechanism, the oxygen tank compartment 32 and a support 63 and a restraint 64, such as a buckle or Velcro strap, for an oxygen bottle, and a mount 66 for the disposable container 42.

The disposable container 42 is shown in detail in FIGS. 12 and 13 and includes an elongate hollow body 69 made, for example, of inexpensive plastic, having an open funnel-like mouth 71 at its top. A deformable shield 73 can be mounted at the mouth 75 of the funnel-like mouth 71 to permit entry of refuse thereinto but to prevent refuse from falling back out therefrom. The body 69 is also formed with two key-hole slots 77 in its front wall 79 for receiving the bolts 66 to removably mount the containers 42 on the housing 12.

The common security latch mechanism generally indicated at 68 comprises a primary drawer security latch sub-mechanism 70, a med tray compartment security latch sub-mechanism 72, and an I.V. compartment security latch sub-mechanism 74. Each sub-mechanism is shown in a secured state, although for the purpose of illustrating the operation thereof, the med tray container cover is shown both in an unsecured position (solid lines) and in a secured position (phantom lines).

In the common security latch sub-mechanism 68, the drawer security latch sub-mechanism 70 comprises a slide latch 76, a sleeve 78, and a seal tab 80. The sleeve is transversely disposed between the sides 18 and 36 of the crash cart housing 12 and is affixed thereto by bracket and bolt or weld stud assemblies 82 and 84. The bracket and weld stud assembly 84 affixing the sleeve to the left side 36 of the housing comprises mounting bolts 86 which extend beyond the left side wall 88 of the housing and thereby form the mount 66 for the disposable container 42. The bracket and weld stud assembly 82 affixing the sleeve to the right side of the housing comprises studs 90 welded to the U-tube 20 and mated with nuts 92 thereby, increasing the structural rigidity of the housing.

Figure 11:
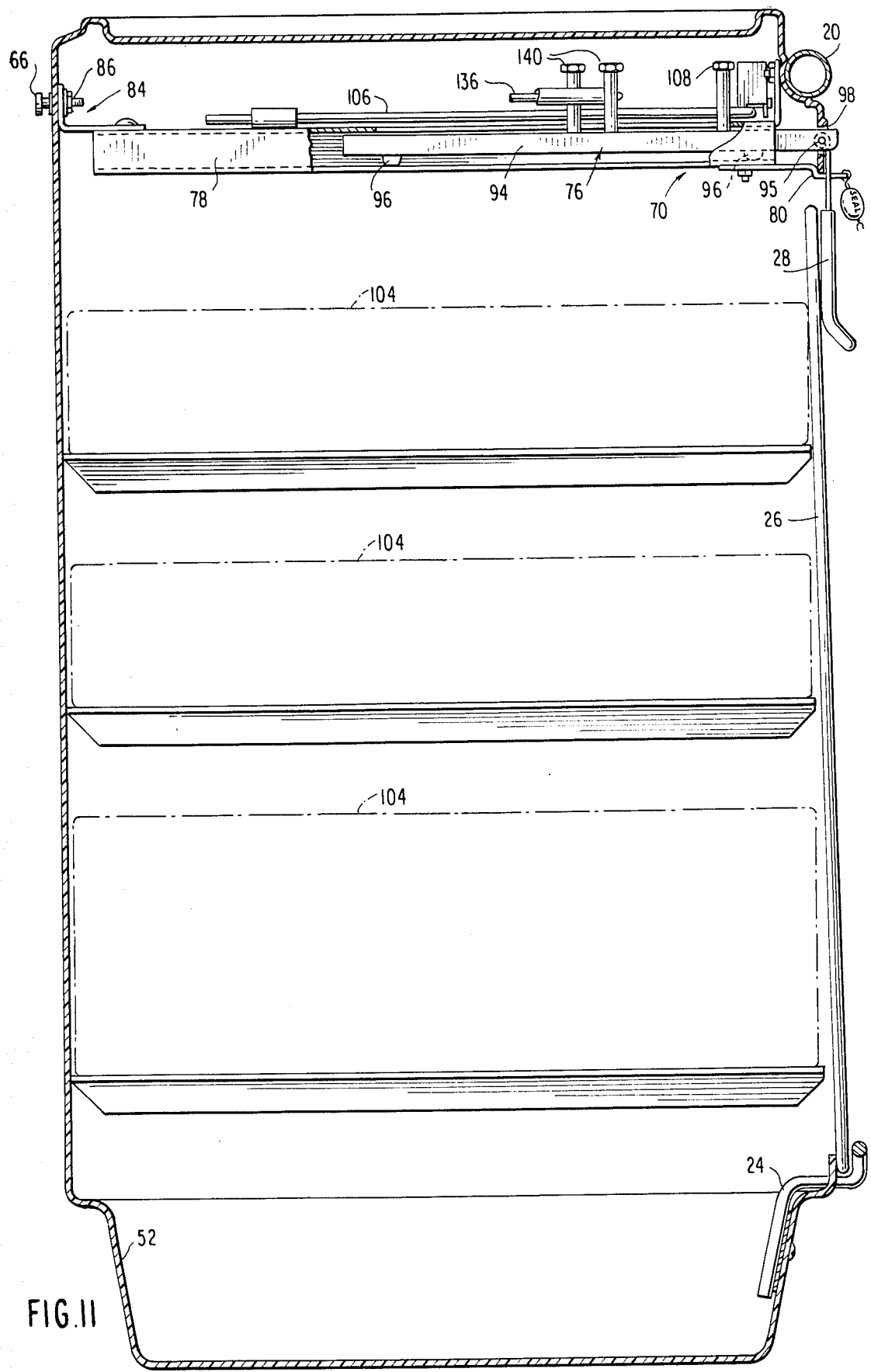
FIG. 11 is a vertical cross-sectional view taken on plane 11—11 in FIG. 4 illustrating an equipment drawer security latch mechanism forming part of the common latch mechanism of the preferred embodiment.

FIG. 11 shows the primary drawer security latch sub-mechanism 70 in partial vertical cross-sectional view. The slide latch 76 comprises a slide member 94 having antifriction feet 96 made of, for example, nylon so that the slide member 94 can easily slide within the interior of the sleeve 78. The slide latch 76 further comprises the locking plate 28, which is hinged by a hinge pin 95 to one end of the slide member 94. During a secured emergency-ready state, the slide member 94 extends past the right extreme of the sleeve and through a small opening 98 in the right side 18 of the housing. The locking plate 28, therefore, can hang from the hinge pin 95 over the seal tab 80 The tab 80 is affixed by bolting to the bottom of the sleeve 78 and extends through the right side of the housing. The locking plate 28 is provided with a shearing slot 100 not shown which fits over and closely conforms to the cross-sectional shape of the seal tab 80 when in the secured emergency-ready state. The seal 54, which may be plastic, is inserted through a hole 102 in the seal tab 80 to maintain the locking plate 28 in the secured position. In the secured emergency-ready state, the cardiac backboard or door 26 is supported by the support bracket 24 disposed at the bottom of the opening 22 on the right side 18 of the housing 12 and is held in the upright position shown in FIG. 11 by the locking plate 28. The cardiac backboard therefore rests between drawers 104 mounted inside the housing 12 and the locking plate 28, securing the drawers 104 and the open top equipment compartment 52 disposed at the bottom of the housing 12 in closed condition.

Referring again to FIG. 3, the med tray compartment security latch sub-mechanism 72 is coupled to the primary drawer sub-mechanism by a positioning rod 106 and position pins 108. The position pins 108 are affixed to the slide member 94 and extend upwardly through an opening 110 in the sleeve 78. A section of the positioning rod 106 having a jog 109 therein is disposed between the positioning pins and another section 111 of the rod 106 is linked to a cover locking bracket 112 of the med tray compartment security latch sub-mechanism 72.

FIGS. 4 and 5 illustrate the common security latch mechanism 68 of FIG. 3 in the unsecured emergency-application state. In FIG. 4, the locking plate 28 has been lifted to a vertical position, thereby shearing the seal 54, and has been translated into the sleeve thereby translating the slide member 94 toward the left side 36 of the housing 12. The positioning pins 108 thus have translated toward the left side causing the jog 109 in the section 107 of the rod 106 thereby to be translated toward the front side 16 of the housing. The cover locking bracket 112 coupled to the section 111 of the rod 106 is thus drawn in the direction of the front side of the housing. As shown in FIG. 5, the cover locking bracket 112 is provided with front and rear bracket guide slots 118 and 120 which accommodate respective bracket guides 122 and 124, the guide 122 being formed by one of the bolts holding the sleeve support bracket 82. The front bracket guide slot 118 extends in a horizontal plane. However, the rear bracket guide slot 120 is inclined. Therefore, as the cover locking bracket 112 translates toward the front side 16 of the housing 12, it also translates in a downward fashion due to interaction of rear guide 124 and the inclined rear bracket guide slot 120. In this manner, a med tray cover lock pin 126 secured approximately in the center of the locking bracket 112 is withdrawn from a hook 128 of the med tray compartment cover 46 as clearly shown by phantom and solid lines in FIGS. 3 and 5. FIG. 6 shows the med tray compartment cover in the secured position. The hook 128 of the med tray compartment cover extends through an opening 130 in the tray wall 132 into a cavity 134 therein and the med tray cover locking pin affixed to the cover locking bracket 112 is inserted into the hook thereby securing the med tray compartment cover in a closed state when the locking bracket 112 is moved toward the rear 30 of the housing and upwardly by reverse movement of the slide member 94.

Figure 7:
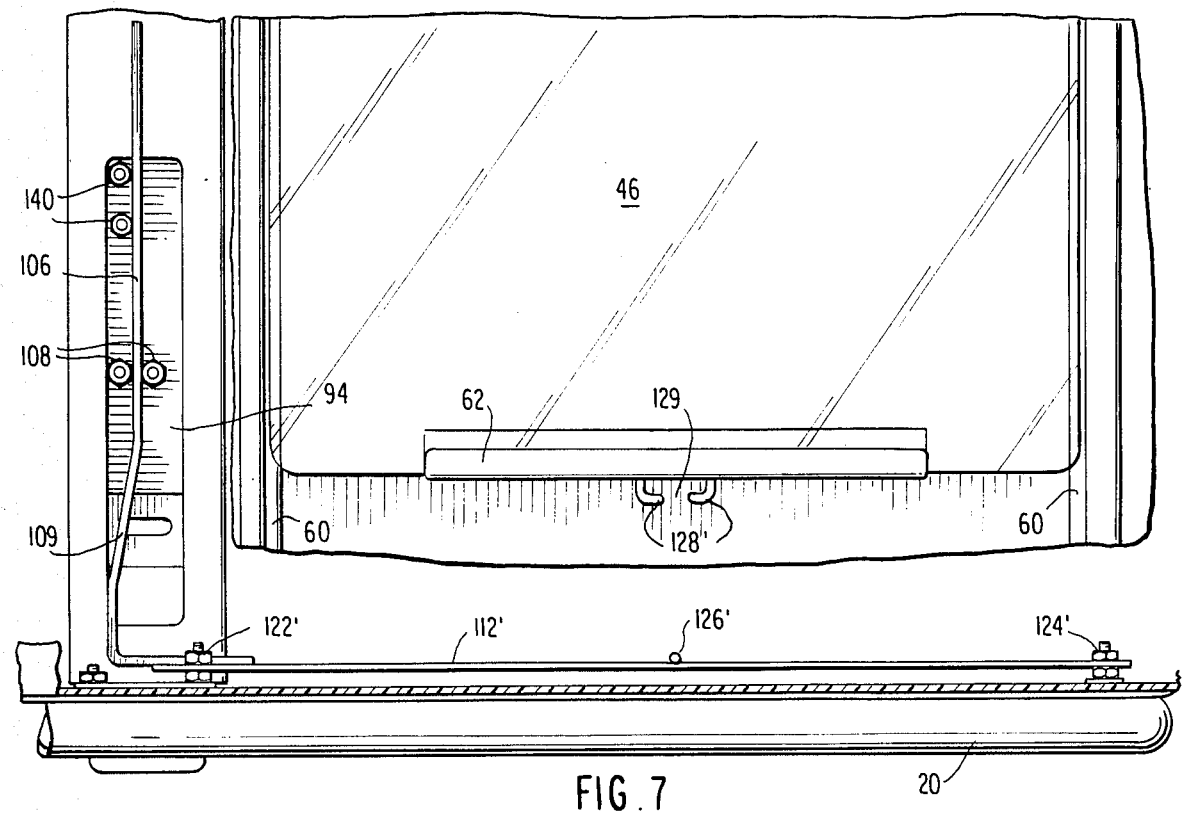
FIGS. 7 and 8 respectively are a top plan and partially broken away view and a vertical cross-sectional view of an alternative embodiment of a portion of the security latch mechanism.
Figure 8:
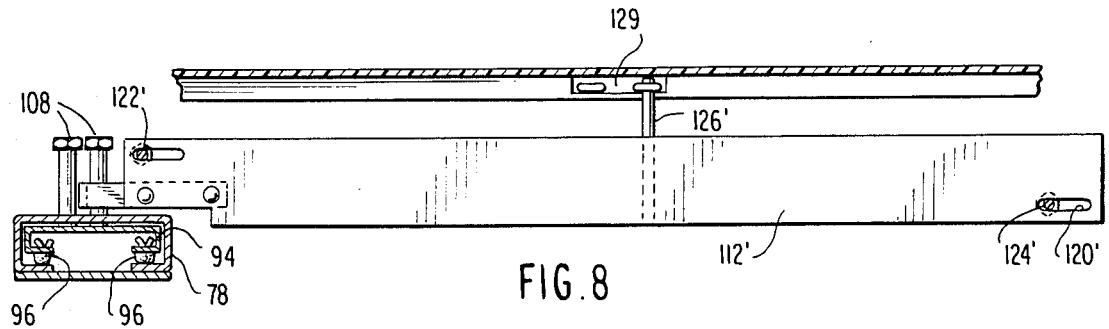

FIGS. 7 and 8 illustrate an alternative embodiment of the med tray compartment security mechanism. In this embodiment, the hook 128' affixed to the med tray compartment cover is segmented, having a gap 129 for accommodating a med tray cover locking pin 126'. In this manner, the cover locking bracket needs only to be translated in a horizontal plane, as shown in FIG. 8. The rear bracket guide slot 120' is therefore cut horizontally, such that the bracket translates horizontally on the forward and rear bracket guides 122' and 124'. In other respects the med tray compartment security mechanism is the same as that previously described.

Figure 9:
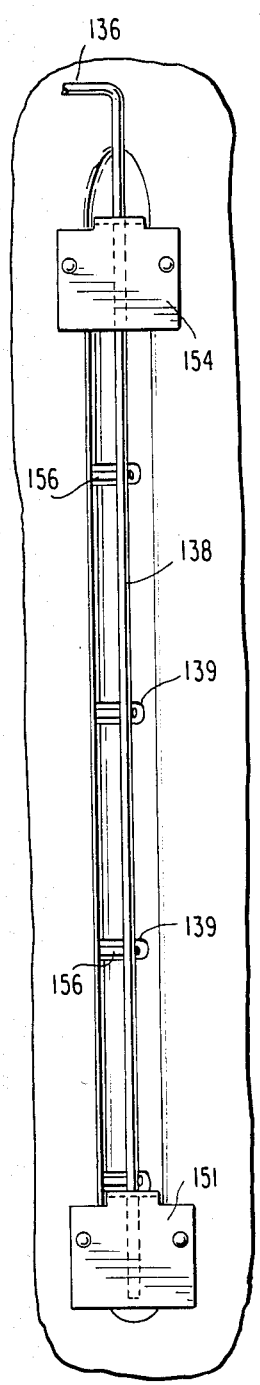
FIGS. 9 and 10 respectively are a side view and a vertical cross-sectional view taken on plane 10—10 in FIG. 4 of I.V. solution compartments and a security latch mechanism therefor forming part of the common latch mechanism of the preferred embodiment.

Referring now to FIGS. 3, 4, 9, and 10, the I.V. compartment security latch sub-mechanism 74 includes a pivot rod 136 pivotable about a vertical shaft 138. As seen in FIG. 9, the vertical shaft 138 is mounted for pivoted movement on a lower mounting bracket 151 and an upper mounting bracket 154 secured to the front of the housing. A second pair of positioning pins 140 is affixed to the slide member 94 and the rod 136 projects therebetween. When the primary drawer security latch sub-mechanism 70 is operated, i.e., when the slide member 94 slides to toward the left side 36 of the housing 12, the rod 136 and shaft are rotated in the counter clockwise direction as seen in FIGS. 3 and 4.

Figure 10:
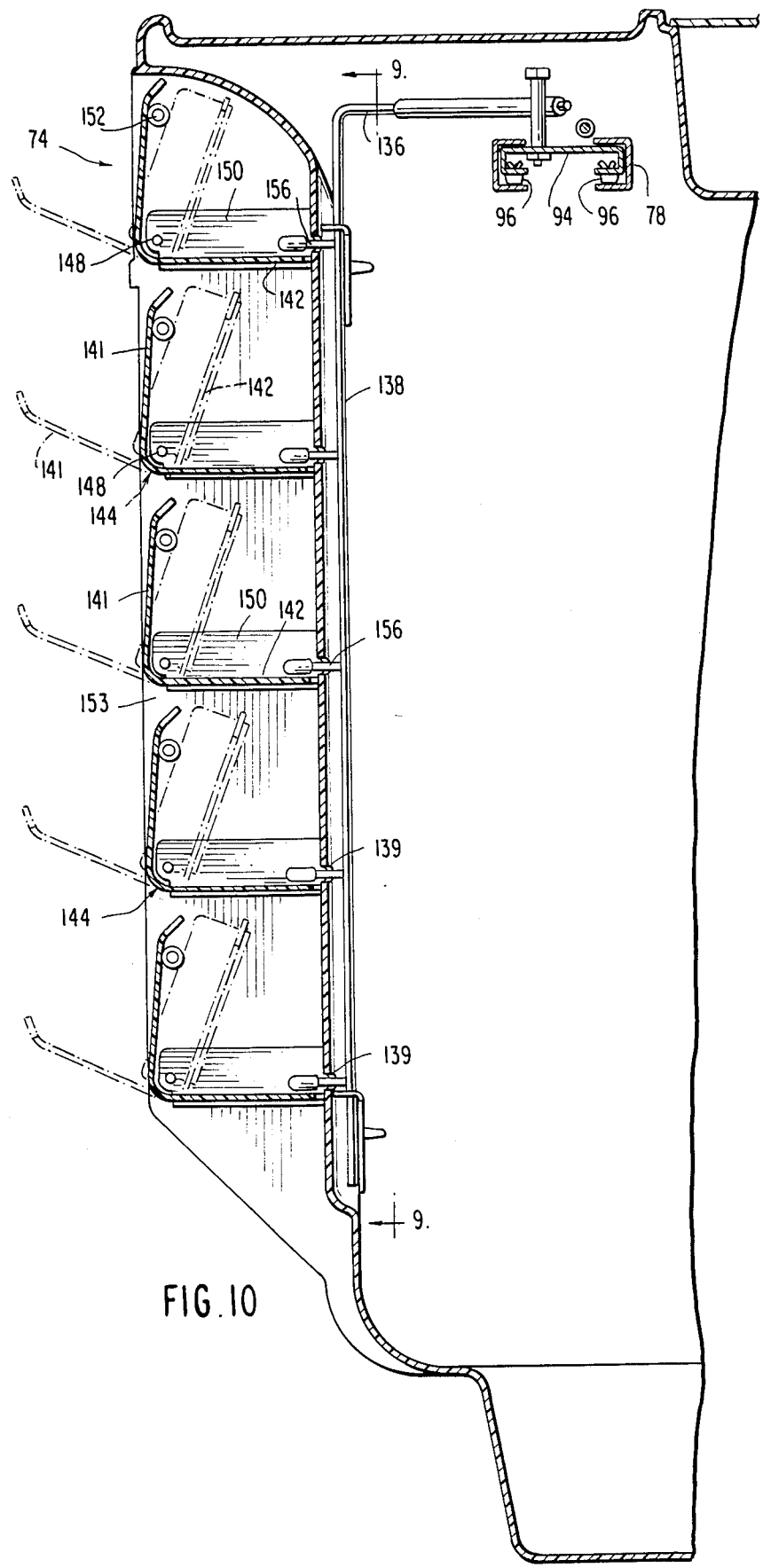

As best seen in FIG. 10, each I.V. compartment 74 comprises a structure having front and bottom walls 141 and 142 joined at an apex 144. Each structure is pivoted within a recess 146 formed in the front side 16 of the housing 12 of the crash cart, on pivot pins 148. Each IV. compartment also has a pair of side walls 150 on which the respective pivot pins 148 are mounted. Stops 152 are mounted on the interior side walls 153 of the recess 146 to abut the side wall 150 when a compartment 74 is in the open position (phantom lines in FIG. 10) and to abut the front wall 140 when a compartment is in the closed position (solid lines in FIG. 10). In the open positions of each compartment, the front wall 140 is held at an angle inclined downwardly toward the housing so that an I.V. container does not fall therefrom.

A number, equal to the number of I.V. compartments 74, of lock tabs 156 are secured, for example, by welding, to project radially from the vertical shaft 138 through mating holes 139 in the front side of the housing. In the locked position shown in FIGS. 3 and 10, these lock tabs overlie the bottom wall 142 of each I.V. compartment to hold each I.V. compartment in its closed position. However, when the primary drawer security latch sub-mechanism 70 is moved to its open position as described above, the pivot rod 136 is rotated in the counter-clockwise direction (as seen in FIGS. 3 and 4) causing the vertical shaft 138 and lock tabs 156 also to rotate in the counter-clockwise direction thereby freeing each I.V. compartment for pivoted movement as described above. In this way, access to the contents of each I.V. compartment is provided.

Of course, to lock the I.V. compartments, they all are first closed and the primary drawer security latch sub-mechanism 70 is then drawn to its forward position moving the slide member 94 toward the right side 18 of the crash cart 10, in turn rotating the rod 136, vertical shaft 138, and lock tabs 156 in a clockwise direction such that the lock tabs overlie the extreme of each second wall 142 of the I.V. compartments.

The caster direction-locking mechanism for locking and unlocking the two rearmost swivel casters 14A and 14B of the crash cart 10 of the present invention will now be described with reference to FIGS. 14 through 18.

As can be seen there, the rearmost swivel casters 14A and 14B are respectively secured for swiveling movement in the rearmost leg of the U-tube 20 and the rear support tube 38. Each caster includes a shaft (not shown), extending into and secured in the respective support tube, and is supported by a bearing (not shown) that permits swivelling movement. The caster further includes a generally U-shaped horn 158 having a base 159 from which the unshown shaft projects and having a horizontal axle 160 spanning the legs 162 of the horn at a position vertically offset from the axis of the supporting tube. A wheel 164 is supported for rotational movement on each axle 160.

The caster direction-locking mechanism includes the operator's handle 34, which may be rotationally or blow molded, for example, and which is mounted for pivoted movement on a horizontally extending hollow shaft 166 rotatably secured in a recess 168 in the rear side 36 of the housing 12. The handle 34 includes an arm 169 projecting from the shaft 166 and a pair of grips 171 (FIG. 2) that can be manipulated by an operator. A handle lock release bar 170 is mounted for reciprocal movement within the handle and includes a pair of legs 172 that pass through the shaft 166 in a direction perpendicular to the axis of the shaft. The extremes of the legs 172 constitute handle locking pins 174 that project through an abutment plate 175 secured to the handle 34 in the region of the shaft 166. A retainer pin 176 passes through each leg 172 of the handle lock release bar 170 and a biasing spring 178 is compressed between the retainer pin and a confronting surface 180 of the handle. Thus, as is apparent from FIGS. 14 and 15, the biasing springs 178 urge the handle locking pins 174 to their projected positions. Similarly, the portion 179 of the bar spanning the legs 172 can be pulled to withdraw the pins 174 against urging of the springs 178.

A handle locking bracket 182 is secured to the inner wall 184 of the recess 168 in the rear side 36 of the housing. This bracket includes an extension 186 that is inclined downwardly at an acute angle from that portion of the bracket 182 secured to the housing. A pair of locking holes 188 is formed in the extension 186 and each registers with the handle locking pins 174. Thus, as can be seen from a comparison of FIGS. 14 and 15, the handle may be rotated in a counter clockwise direction from its depending or caster unlocking position (FIG. 14) to an upstanding or caster locking position (FIG. 15) during which the handle locking pins 174 engage the extension 186 of the handle locking bracket 182. This engagement urges the locking pins 174 and hence the handle lock release bar 170 to move in a direction opposite that urged by the biasing springs 178. When the pins 174 are registered with the locking holes 188 of the extension 186, the force exerted by the biasing springs 178 causes the pins and handle release bar to return to their rest position with the pins projecting into the holes. Thus, the handle is locked in its upright position.

The handle may be released from the locked position by pulling the portion 179 against the force of the biasing springs to withdraw the locking pins 174 from the holes 188 and thereafter by rotating the handle in a clockwise direction as seen in the figures again to its retracted position.

Referring now to FIG. 17, it will be seen that the shaft 166 has a cam 190 attached to it. This cam is positioned to engage a lifter bracket 192 that is mounted for pivoted movement about a pivot pin 194 secured in the interior of the crash cart housing 12. When so engaged, and as seen in FIG. 17, the lifter bracket is rotated in a clockwise direction to urge the free end therof upwardly.

The lifter bracket is coupled to a lifter rod 196 that is guided through an opening 198 formed in an inclined section 200 of the rear wall of the housing. The extreme of the lifter rod opposite that coupled to the lifter bracket is connected to one end of a coupling rod 202 mounted for pivoted movement at the bottom of the housing in a pair of pivot brackets 204, as seen in FIG. 18. Thus, when the lifter rod is lifted by interaction of the cam 190 and the lifter bracket 192, the coupling rod 202 is rotated in a clockwise direction as seen in FIG. 17.

Each extreme of the coupling rod is formed with a jog 206 and an extension 208 that mates with an aperture in a D-shaped collar support lever 210 as shown in FIG. 18. Each support lever 210 is mounted for pivoted movement about a pivot pin 212 secured to the housing of the crash cart. A coil spring 220 is carried on each pivot pin 212 as shown in FIG. 18 and is arranged to urge the free end of each support lever downwardly. It will be appreciated that when the lifter rod 196 is lifted as described above, the coupling rod will be rotated in the clockwise direction also to rotate the support levers 210 in a clockwise direction.

Each support lever carries a D-shaped collar at its free end. Each D-shaped collar 214 encircles one of the support tubes at the rear of the crash cart just above the horn 158 of the associated caster.

The flat side 216 of each D-shaped collar 214 is formed with a caster-locking notch 218 as shown clearly in FIG. 16.

When the handle 34 is in its steering position shown in FIG. 15, the cam 190 is disengaged from the lifter bracket 192. Accordingly, the support levers 210 are permitted to rotate under the influence of gravity and the coil springs 220 in a counter-clockwise direction as seen in FIG. 17 thereby permitting the D-shaped collars first to ride on the base 159 of each horn of each rear caster. However, when each rear caster reaches a position shown in FIGS. 15 and 16, again under the influence of gravity the D-shaped collars will rotate further in the counter-clockwise direction permitting the notches 218 to engage and embrace the side surfaces of the legs 162 of the horns 158 thereof. In this way, each of the wheels of the rear casters will be locked in parallel planes in the direction of movement of the crash cart i.e. with their respective axels 160 in mutually parallel relation. These locked casters can then serve as pivots to aid high speed maneuverability of the cart 10. However, when the handle is returned to its retracted position shown in FIG. 14, the cam 190 engages the lifter bracket 192 to lift the support levers 210 and attached D-shaped collars 214 thereby disengaging the notches from embrace of the horns of the rear casters. Accordingly, these rear casters are again permitted to swivel freely to permit easy maneuverability of the crash cart in tight spaces.

It will be readily seen from the description set forth above that the crash cart of the present invention provides many advantages which include the following:

1. Easy visual confirmation that the crash cart has a full complement of critical equipment and supplies.
2. Easy access to all compartments of the crash cart which are nevertheless securely sealed simultaneously in an emergency-ready condition by a locking mechanism operable by a single locking plate.
3. Provision of a simple, easily operated mechanism for locking the two rear swivel casters of the cart for relation in the single direction of movement of the cart so that the cart may be quickly and easily maneuvered but further provision of easy release of these swivel casters for easy maneuverability in tight spaces.

Although specific embodiments of the present invention have been described above in detail, it will be understood that this description is for purposes of understanding. Modification of the preferred embodiments described herein may be made by those skilled in the art without departing from the scope of the present invention which is set forth in the following claims.

What is claimed is:

1. An emergency crash cart, comprising:
housing means having a top formed with a recessed tray for storing instruments, supplies, and the like, and at least one side having an opening therein;
cover means including a first engaging portion, for selectably covering said tray but providing access to the interior thereof when removed therefrom;
removable door means enclosing said opening in said one side; and
latch means for simultaneously locking said cover means in position covering said tray and locking said door means in position enclosing said opening, said latch means including a slide member slidable between a locking position and an unlocking position, a second engaging portion, and coupling means for coupling sliding movement of said sliding member to said second engaging portion, said cover means being locked by mutual engagement of said first and second engaging portions.

2. An emergency crash cart according to claim 1, wherein said first engaging portion comprises hook means, and said second engaging portion comprises a lock pin for selectably engaging said hook means, said slide member being operable from the exterior of said housing and being movable between a first position in which said lock pin is engaged with said hook means by action of said coupling means, and a second position in which said lock pin is disengaged from said hook means by action of said coupling means.

3. An emergency crash cart according to claim 2, further comprising:
   means for supporting said removable door means at a bottom edge thereof, and
   a locking plate coupled to said slide member, said locking plate being movable, when said slide member is in said first position, to a depending position overlying and capturing the top edge of said removable door means, and to a release position not overlying the top edge of said door means, said locking plate being manipulable in the release position to move said slide member from the first to the second position.

4. An emergency crash cart according to claim 3, further comprising:
   a tab fixedly mounted with said housing, said locking plate being formed with a shear slot therein having a shape closely conforming to the cross-sectional shape of said tab, for receiving said tab when said locking plate is in the depending position; and
   breakable seal means engagable with said tab to hold said locking plate in the depending position but being breakable by interaction of said tab and said locking plate when said locking plate is moved to the release position.

5. An emergency crash cart according to claim 2, further comprising:
   a locking plate coupled to said slide member, said locking plate being movable, when said slide member is in said first position, to a depending position, and to a release position in which it is manipulable to move the slide member from the first to the second position;
   a tab fixedly mounted with said housing, said locking plate being formed with a shear slot therein having a shape closely conforming to the cross-sectional shape of said tab, for receiving said tab when said locking plate is in the depending position; and
   breakable seal means engagable with said tab to hold said locking plate in the depending position but being breakable by interaction of said tab and said locking plate when said locking plate is moved to the release position.

6. An emergency crash cart according to claim 2, further comprising:
   a cover locking bracket, upon which said lock pin is mounted, mounted for lateral and upward and downward translational movement; lateral movement thereof in one direction causing simultaneous upward movement thereof to engage said lock pin with said hook means, and lateral movement thereof in a direction opposite the one direction causing downward movement thereof to disengage said lock pin from said hook means.

7. An emergency crash cart according to claim 6, wherein said slide plate is mounted for movement in a direction generally perpendicular to the direction of lateral movement of said cover locking bracket, and wherein said coupling means comprises a positioning rod having one section extending in the direction of lateral movement of said cover locking bracket and linked to said cover locking bracket, and a second section, having a jog therein, extending generally in the direction of movement of said slide member; said slide member including means for embracing said second section whereby movement of said slide member causes said embracing means to shift said positioning rod by interaction with said jog thereby moving said first section in the lateral direction of said cover locking bracket.

8. An emergency crash cart according to claim 2, further comprising:
   a cover locking bracket, upon which said lock pin is mounted, mounted for lateral movement in one direction and in an opposite direction between rest and locked positions and wherein
   said hook means is formed with a gap for receiving said lock pin when said cover locking bracket is in the rest position and said cover is moved to the closed position, and wherein said lock pin lockingly engages said hook means when said cover locking bracket is in the locked position.

9. An emergency crash cart according to claim 8, wherein said slide member is mounted for movement in a direction generally perpendicular to the direction of lateral movement of said cover locking bracket, and wherein said coupling means comprises a positioning rod having one section extending in the direction of lateral movement of said cover locking bracket and linked to said cover locking bracket, and a second section, having a jog therein, extending generally in the direction of movement of said slide member; said slide member including means for embracing said second section whereby movement of said slide member causes said embracing means to shift said positioning rod by interaction with said jog thereby moving said first section in the lateral direction of said cover locking bracket.

10. An emergency crash cart according to claim 1, further comprising at least one drawer mounted within said housing and accessible through said opening in said one side, wherein said housing is formed with a recessed equipment compartment in its bottom accessible through said opening in said one side below said drawer.

11. An emergency crash cart according to claim 1, wherein said housing is formed with at least one recessed prep area adjacent said tray.

12. An emergency crash cart according to claim 1, further comprising a disposable container for refuse and means for removably mounting said container on one side of said housing.

13. An emergency crash cart according to claim 12, wherein said disposable container is formed with a funnel-like opening for receiving refuse and further comprises means for permitting refuse to enter said funnel-like opening but for preventing refuse from passing back therethrough.

14. An emergency crash cart, comprising:
   housing means having a top formed with a recessed tray for storing instruments, supplies, and the like, and at least one side having an opening therein;

cover means for selectably covering said tray but providing access to the interior thereof when removed therefrom;
a removable door means enclosing said opening in said one side; and
latch means for simultaneously locking said cover means in position covering said tray and said door means in position enclosing said opening,
wherein one side of said housing is formed with a compartment for receiving a tank of oxygen or the like and further comprises means for supporting the tank and means for restraining the tank within said compartment.

15. An emergency crash cart, comprising:
housing means having a top formed with a recessed tray for storing instruments, supplies, and the like;
cover means including a first engaging portion, for selectably covering said tray but providing access to the interior thereof when removed therefrom;
at least one compartment mounted on one side of said housing means and being pivotable between an open position providing access to its interior and a closed position with its interior enclosed; and
latch means for simultaneously locking said cover means in position covering said tray and said compartment in said closed position, said latch means including a slide member slidable between a locking position and an unlocking position, a second engaging portion, and coupling means for coupling sliding movement of said sliding member to said second engaging portion, said cover means being locked by mutual engagement of said first and second engaging portions.

16. An emergency crash cart according to claim 15, wherein said first engaging portion comprises hook means, and said second engaging portion comprises a lock pin for selectably engaging said hook means, said slide member being operable from the exterior of said housing and being movable between a first position in which said lock pin is engaged with said hook means by action of said coupling means, and a second position in which said lock pin is disengaged from said hook means by action of said coupling means.

17. An emergency crash cart according to claim 16, further comprising:
a cover locking bracket, upon which said lock pin is mounted, mounted for lateral and upward and downward translational movement; lateral movement thereof in one direction causing simultaneous upward movement thereof to engage said lock pin with said hook means, and lateral movement thereof in a direction opposite the one direction causing downward movement thereof to disengage said lock pin from said hook means.

18. An emergency crash cart according to claim 17, wherein said slide plate is mounted for movement in a direction generally perpendicular to the direction of lateral movement of said cover locking bracket, and wherein said positioning link means comprises a positioning rod having one section extending in the direction of lateral movement of said cover locking bracket and linked to said cover locking bracket, and a second section, having a jog therein, extending generally in the direction of movement of said slide member; said slide member including means for embracing said second section whereby movement of said slide member causes said embracing means to shift said positioning rod by interaction with said jog thereby moving said first section in the lateral direction of said cover locking bracket.

19. An emergency crash cart according to claim 16, further comprising:
a cover locking bracket, upon which said lock pin is mounted, mounted for lateral movement in one direction and in an opposite direction between rest and locked positions; and wherein
said hook means is formed with an opening for receiving said lock pin when said cover locking bracket is in the rest position and where in said lock pin lockingly engages said hook means when said cover locking bracket is in the locked position.

20. An emergency crash cart according to claim 19, wherein said slide plate is mounted for movement in a direction generally perpendicular to the direction of lateral movement of said cover locking bracket, and wherein said coupling means comprises a positioning rod having one section extending in the direction of lateral movement of said cover locking bracket and linked to said cover locking bracket, and a second section, having a jog therein, extending generally in the direction of movement of said slide member; said slide member including means for embracing said second section whereby movement of said slide member causes said embracing means to shift said positioning rod by interaction with said jog thereby moving said first section in the lateral direction of said cover locking bracket.

21. An emergency crash cart according to claim 15, wherein said one side of said housing is formed with a recess and wherein said compartment comprises a bottom wall and a front wall generally perpendicular to said bottom wall, said compartment being mounted for pivoted movement within said recess between an open position with said front wall tilted outwardly from said recess to provide access to said compartment and a closed position with said front wall enclosing said compartment and at least a portion of said recess; and further comprising stop means for limiting pivoted movement of said compartment at both the open and closed positions.

22. An emergency crash cart according to claim 21, wherein said latch means includes lock tab means for engaging said bottom wall of said compartment when in the closed position for locking said compartment in the closed position.

23. An emergency crash cart according to claim 22, wherein said latch means further comprises:
link means for linking said slide member to said lock tab; said slide member being movable between a first position in which said lock tab is moved through said link means to engage said bottom wall of said compartment and a second position in which said lock tab is moved through said link means to disengage from said bottom wall of said compartment.

24. An emergency crash cart according to claim 23, wherein said lock means includes a rotatable shaft from which said lock tab radially projects and a pivot rod also projecting radially from said shaft; and wherein said slide member includes means for embracing said pivot rod for causing pivoted movement thereof when said slide member is moved between the first and second positions.

25. An emergency crash cart according to claim 15, wherein said housing is formed with an opening in a side thereof and with a recessed equipment compartment in its bottom accessible through said opening.

26. An emergency crash cart according to claim 15, wherein said housing is formed with at least one recessed prep area adjacent said tray.

27. An emergency crash cart according to claim 15, further comprising a disposable container for refuse and means for removably mounting said container on one side of said housing.

28. An emergency crash cart according to claim 27, wherein said disposable container is formed with a funnel-like opening for receiving refuse and further comprises means for permitting refuse to enter said funnel-like opening but for preventing refuse from passing back therethrough.

29. An emergency crash cart, comprising:
  housing means having a top formed with a recessed tray for storing instruments, supplies, and the like;
  cover means for selectably covering said tray but providing access to the interior thereof when removed therefrom;
  at least one compartment mounted on one side of said housing means and being pivotable between an open position providing access to its interior and a closed position with its interior enclosed; and
  latch means for simultaneously locking said cover means in position covering said tray and said compartment in said closed position,
  wherein a side of said housing is formed with a compartment for receiving a tank of oxygen or the like and further comprises means for supporting the tank and means for restraining the tank within said compartment.

30. An emergency crash cart comprising:
  housing means having a top formed with a recessed tray for storing instruments, supplies, and the like, and at least one side having an opening formed therein;
  cover means for selectably covering said tray but providing access to the interior thereof when removed therefrom;
  at least one drawer mounted within said housing and accessible through said opening in said one side;
  removable door means enclosing said opening in said one side:
  at least one compartment mounted on another side of said housing and being pivotable between an open position providing access to its interior and a closed position with its interior enclosed; and
  latch means for simultaneously locking said cover means in position covering said tray, said door means in position enclosing said opening, and said compartment in the closed position.

31. An emergency crash cart according to claim 30, wherein said cover means, includes hook means, and wherein said latch means includes a slide member operable from the exterior of said housing, a lock pin for selectably engaging said hook means, and coupling means for coupling said slide member to said lock pin, said slide member being movable between a first position in which said lock pin is engaged with said hook means by action of said coupling means, and a second position in which said lock pin is disengaged from said hook means by action of said coupling means.

32. An emergency crash cart according to claim 31, further comprising:
  means for supporting said removable door means at a bottom edge thereof, and
  a locking plate coupled to said slide member, said locking plate being movable, when said slide member is in said first position, to a depending position overlying and capturing the top edge of said removable door means, and to a release position not overlying the top edge of said door means, said locking plate being manipulable in the release position to move said slide member from the first to the second position.

33. An emergency crash cart according to claim 32, further comprising:
  a tab fixedly mounted with said housing, said locking plate being formed with a shear slot therein having a shape closely conforming to the cross-sectional shape of said tab, for receiving said tab when said locking plate is in the depending position; and
  breakable seal means engagable with said tab to hold said locking plate in the depending position but being breakable by interaction of said tab and said locking plate when said locking plate is moved to the release position.

34. An emergency crash cart according to claim 31, further comprising:
  a cover locking bracket, upon which said lock pin is mounted, mounted for lateral and upward and downward translational movement; lateral movement thereof in one direction causing simultaneous upward movement thereof to engage said lock pin with said hook means, and lateral movement thereof in a direction opposite the one direction causing downward movement thereof to disengage said lock pin from said hook means.

35. An emergency crash cart according to claim 34, wherein said slide plate is mounted for movement in a direction generally perpendicular to the direction of lateral movement of said cover locking bracket, and wherein said coupling means comprises a positioning rod having one section extending in the direction of lateral movement of said cover locking bracket and linked to said cover locking bracket, and a second section, having a jog therein, extending generally in the direction of movement of said slide member; said slide member including means for embracing said second section whereby movement of said slide member causes said embracing means to shift said positioning rod by interaction with said jog thereby moving said first section in the lateral direction of said cover locking bracket.

36. An emergency crash cart according to claim 30, wherein one side of said housing is formed with a compartment for receiving a tank of oxygen or the like and further comprises means for supporting the tank and means for restraining the tank within said compartment.

37. An emergency crash cart according to claim 30, further comprising a disposable container for refuse and means for removably mounting said container on one side of said housing.

38. An emergency crash cart according to claim 37, wherein said disposable container is formed with a funnel-like opening for receiving refuse and further comprises means for permitting refuse to enter said funnel-like opening but for preventing refuse from passing back therethrough.

* * * * *

UNITED STATES PATENT AND TRADEMARK OFFICE
CERTIFICATE OF CORRECTION

PATENT NO. : 4,790,610

DATED : December 13, 1988

INVENTOR(S) : ROBERT J. WELCH, ET AL.

It is certified that error appears in the above-identified patent and that said Letters Patent is hereby corrected as shown below:

IN [56] REFERENCES CITED

U.S. PATENT DOCUMENTS, "224,294 2/1980 Koch" should read --224,294 2/1880 Koch--.

COLUMN 6

Line 8, "unsecurred" should read --unsecured--.
    Line 37, "tab 80 The" should read --tab 80. The--.

COLUMN 7

Line 64, "IV." should read --I.V.--.

COLUMN 9

Line 12, "counter clockwise" should read --counterclockwise--.
    Line 37, "therof" should read --thereof--.

UNITED STATES PATENT AND TRADEMARK OFFICE
CERTIFICATE OF CORRECTION

PATENT NO. : 4,790,610

DATED : December 13, 1988

INVENTOR(S) : ROBERT J. WELCH, ET AL.

It is certified that error appears in the above-identified patent and that said Letters Patent is hereby corrected as shown below:

COLUMN 10

Line 16, "axels 160" should read --axles 160--.

COLUMN 14

Line 11, "where in" should read --wherein--.

Signed and Sealed this

Second Day of January, 1990

Attest:

JEFFREY M. SAMUELS

Attesting Officer

Acting Commissioner of Patents and Trademarks